United States Patent [19]
Bradshaw et al.

[11] Patent Number: 5,782,741
[45] Date of Patent: Jul. 21, 1998

[54] TWO-STAGE TREATMENT WIRE

[75] Inventors: Anthony J. Bradshaw, Missouri City; Kenneth M. Bueche, Friendswood, both of Tex.

[73] Assignee: Guidant Coropration, Santa Clara, Calif.

[21] Appl. No.: 746,467

[22] Filed: Nov. 12, 1996

[51] Int. Cl.⁶ ............................................. A61N 5/00
[52] U.S. Cl. ................................................. 600/3
[58] Field of Search ..................... 600/1–8; 128/656–659

[56] References Cited

U.S. PATENT DOCUMENTS

| | | | |
|---|---|---|---|
| 4,819,618 | 4/1989 | Liprie | 600/7 |
| 4,819,751 | 4/1989 | Shimada et al. | 128/344 |
| 4,861,520 | 8/1989 | Van't Hooft | 252/644 |
| 4,909,781 | 3/1990 | Husted | 604/22 |
| 5,084,002 | 1/1992 | Liprie | 600/7 |
| 5,135,535 | 8/1992 | Kramer | 606/194 |
| 5,199,939 | 4/1993 | Kake et al. | 600/3 |
| 5,238,004 | 8/1993 | Sahatjian et al. | 128/772 |
| 5,282,781 | 2/1994 | Liprie | 600/3 |
| 5,302,168 | 4/1994 | Hess | 600/3 |
| 5,411,476 | 5/1995 | Abrams et al. | 604/95 |
| 5,456,680 | 10/1995 | Taylor et al. | 606/2 |
| 5,503,613 | 4/1996 | Weinberger | 600/3 |
| 5,503,614 | 4/1996 | Liprie | 600/7 |

FOREIGN PATENT DOCUMENTS 9519807  7/1995  WIPO ............................... A61N 5/00

*Primary Examiner*—John P. Lacyk
*Attorney, Agent, or Firm*—Arnold, White & Durkee

[57] ABSTRACT

A treatment wire is provided for the delivery of a treatment to a site within the body that is composed of two stages. This treatment wire includes a single wire drive portion that is optimal for the proximal end of the treatment wire and engages any storage and/or drive mechanism that may be used in storing and/or deploying the treatment wire. The single drive wire is ground at its distal end to a smaller diameter and encased within a tube forming the second stage of the treatment wire. Because the drive wire terminates proximally to the tube, a cavity is formed that can retain the treating substance to be delivered to the patient. Shape-memory/superelastic material is preferably used for the construction of the treatment wire. When such material is used, the distal end of the treatment wire can be heat treated in order to render it more ductile and, therefore, more desirable for use in the tortuous passageways of the body.

40 Claims, 1 Drawing Sheet

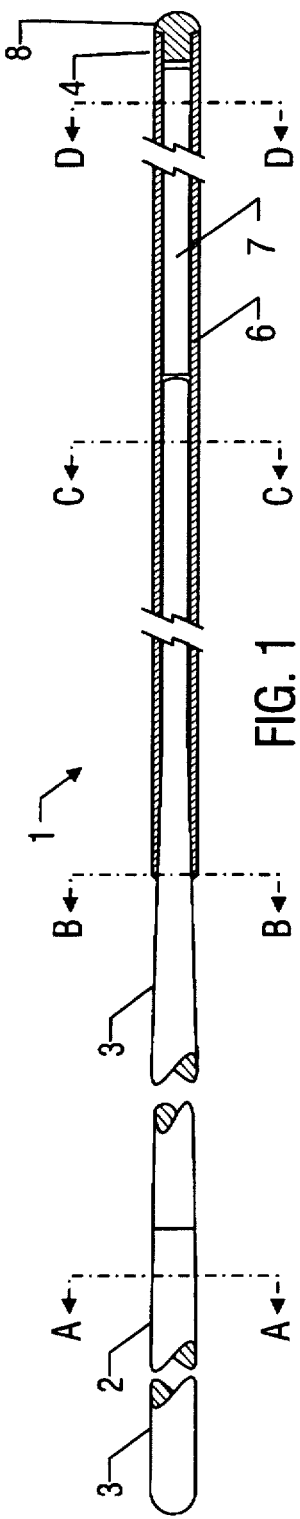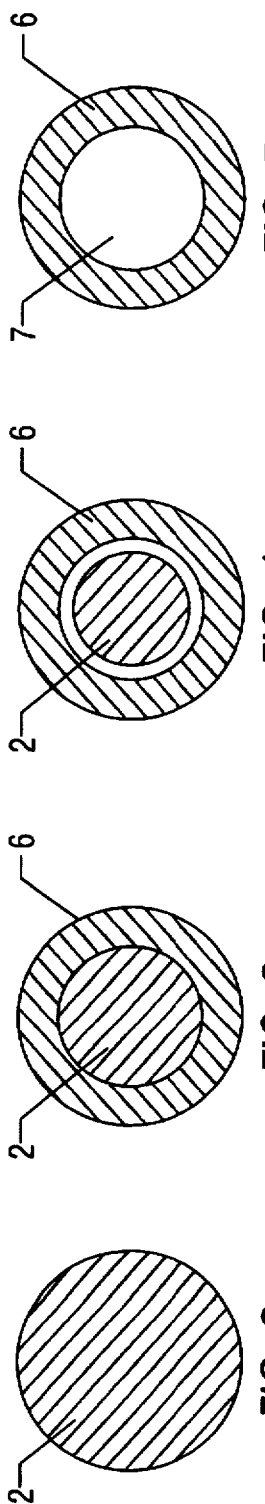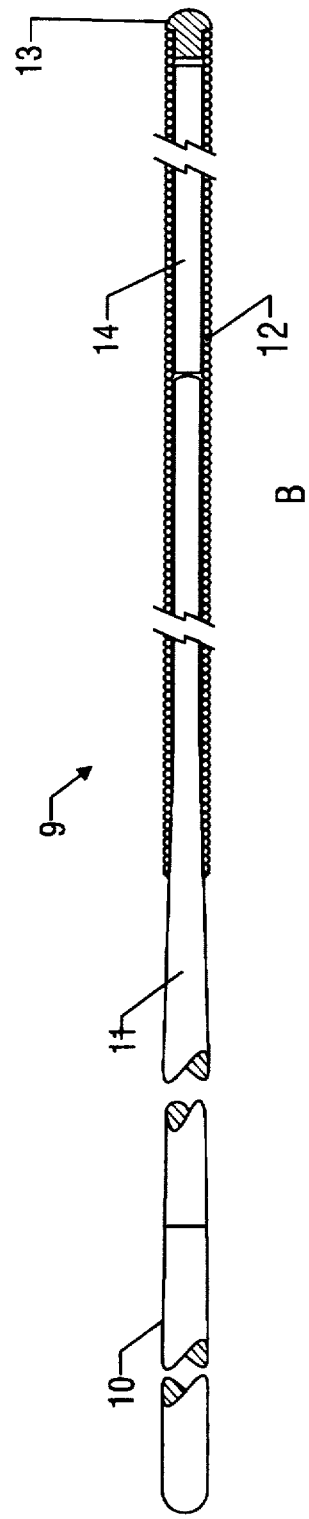

TWO-STAGE TREATMENT WIRE

BACKGROUND OF THE INVENTION

The present invention relates to an apparatus and a method to introduce a treatment within the body in order to combat various diseases. For example, any of a number of diseases, including tumors or restenosis after arterial intervention, can be treated through the delivery of radioactive treatment deep within the body.

Conventional radioactive treatment of this sort occurs through the placement of a radioactive source at the locus of the disease. The source is typically attached to a treatment wire that courses to the desired locus through an introducing catheter that in turn is properly disposed within the body through the use of a guidewire. This process is well known in the art and is described for example in U.S. Pat. No. 5,199,939.

There are several treatment wires in the prior art used to carry treatment sources to the disease locus. Examples of such prior art devices are described in U.S. Pat. Nos. 4,819,618; 4,861,520; 5,084,002; 5,141,486; 5,282,781; and 5,503,614.

U.S. Pat. Nos. 4,819,618 and 5,141,486 describe a radioactive source element that is attached to a treatment wire through a junction welded to the treatment wire. This welding technique near the tip of the wire resulted in a relatively inflexible tip and applied severe stresses to the weld because the tip must travel through some of the most sinuous passages that are near the treatment locus.

U.S. Pat. No. 4,861,520 describes a treatment wire that attaches a flexible wire to the radioactive treatment source by means of a stiff capsule welded onto the distal end of the wire. This treatment wire presents a stiff distal end being driven into the body with a more flexible wire. The result can be the highly undesirable formation of kinks in the wire, similar to the concept of "pushing a rope."

The device described in U.S. Pat. No. 5,084,002 has a very thin radioactive source placed in a cavity (hole) drilled longitudinally in the distal end of a solid platinum wire. This assembly is then drawn down to the desired diameter of the wire. The drilling of this hole at in the treatment wire is an expensive and very difficult process. Because the diameter of the treatment wire is only a few thousands of an inch, the drilling of a hole that with a length equal to many time the diameter of wire is tricky and expensive.

U.S. Pat. No. 5,282,781 describes a treatment wire that has a tube and backbone construction coursing through its entire length. A radioactive source is plugged at the end of the wire in a space left because the backbone wire terminates a short distance before the distal end of the tube. This patent describes that the treatment wire is drawn down to a reduced diameter so as to seal the tube, the backbone, and the plug. This "drawing down" was performed in order to prevent flakes from the radioactive source from migrating throughout the inside of the treatment wire and thus contaminating it. This tube and backbone construction, however, is expensive because of the drawing down of the entire wire requires an extra manufacturing step and additional equipment. It also has operational problems because the tube courses through the entire length of the wire and if a failure crack occurs at any point on the tube it is likely to run along the tube's full length and potentially result in the release or loss of radioactive material. When an afterloader is used such failure becomes more likely because the drive mechanism tightly cinches the treatment wire with large compressive forces in order to push it through the catheter. Because the friction between the catheter and the treatment wire can be large due to the length of the treatment wire, a large cinching force is necessary to provide the drive mechanism with sufficient grip in order to propel the treatment wire axially. The tube component of the treatment wire is much more susceptible to failure due to this cinching force than a solid wire by itself would be.

Finally, U.S. Pat. No. 5,503,614 discloses a similar tube and backbone construction to the one in U.S. Pat. No. 5,282,781. This treatment wire is not "drawn down," however, because it specified to be made out of a shape-memory alloy and the radioactive source is encapsulated before it is placed in the distal end of the tube. Because this setup is not drawn down and there is a small annular space between the backbone wire and the tube along the entire length of the treatment wire, it encounters certain operational problems. The friction that results between the outer diameter of the backbone and the inner diameter of the tube from the constant bending and turning of treatment wire causes microscopic flakes to slough off (fretting). This contaminates the space between the two components of the backbone wire and can cause the treatment wire to fatigue prematurely and to behave irregularly when this contaminated portion of the wire is engaged by an afterloader's drive or storage system.

Moreover, this treatment wire retains some of the disadvantages of the wire in U.S. Pat. No. 5,282,781. Since in this case there is space between the backbone wire and the surrounding tube, when the treatment wire is cinched by the drive system or when it is tightly wound for storage on an afterloader spool, the tube will tend to collapse. This causes premature fatigue and the tube will be more likely to fail. And, as was the case with the treatment wire in U.S. Pat. No. 5,282,781, a failure at any point on the tube is likely to run to the entire length of the tube or fracture and fail circumferentially.

SUMMARY OF THE INVENTION

The flexible treatment wire for the treatment of diseases produced by the present invention ameliorates these and other deficiencies present in the prior art. This invention is directed to a flexible treatment wire that contains a treatment source and is maneuverable through the conduits of the body to the locus at which the treatment is to be delivered.

The treatment wire includes a flexible single wire portion that is encased in a flexible tube at its distal end. The tube can be attached to the wire through welding, soldering, or any other appropriate attaching means. The wire terminates before it reaches the distal end of the tube. The treatment source is located at the distal end of the tube and can be locked in place through a variety of means including a plug at the distal end of the tube.

This achieves a desirable long span of the treatment wire being composed of a very flexible single wire portion while at the same time the distal end of the treatment wire is composed of a tube surrounding the wire. In a preferred embodiment of the invention, the single wire and the tube are constructed from nitinol or any other shape-memory/superelastic material.

When the treatment wire is constructed from shape-memory/superelastic material this invention is further improved if the distal end of the treatment wire is treated to have increased deformability. The loss of restorative tendency at the distal end allows the treatment wire to be more easily and with less stress be guided to the treatment locus.

BRIEF DESCRIPTION OF THE DRAWINGS

These and other attributes of this invention are shown in the following drawings:

FIG. 1 is a longitudinal cross-section of the invention showing the components of the treatment wire.

FIG. 2 is a frontal cross-section of the invention taken on the line A—A of FIG. 1; on a larger scale.

FIG. 3 is a frontal cross-section of the invention taken on the line B—B of FIG. 1; on a larger scale.

FIG. 4 is a frontal cross-section of the invention taken on the line C—C of FIG. 1; on a larger scale.

FIG. 5 is a frontal cross-section of the invention taken on the line D—D of FIG. 1; on a larger scale.

FIG. 6 is a longitudinal cross-section of an alternative embodiment of the invention.

DESCRIPTION OF ILLUSTRATIVE EMBODIMENTS

FIGS. 1–5 show an embodiment of the treatment wire 1. A flexible drive wire 2 extends from proximal end 3 of the treatment wire 1 and courses almost to distal end 4 of the treatment wire 1. Proximal end 3 is the area near the tip of the treatment wire that remains outside the body while the wire is being deployed and distal end 4 is the area near the tip of the treatment wire that reaches the locus where the treatment is administered. The diameter of drive wire 2 from proximal end 3 up to neck area 5 can range depending upon the material used but is generally in the range from 0.012" to 0.024".

Flexible drive wire 2 can be made out of any number of flexible materials but it preferably is made from nitinol (nickel/titanium alloys that exhibit shape-memory and related superelasticity) or other shape-memory/superelastic metals, alloys or materials. A drive wire 2 made out of nitinol could range in diameter from 0.010" to 0.028", preferably from 0.014" to 0.024", and more preferably from 0.0175" to 0.0185". Other flexible materials used in the past for such wires have been, but are not limited to, platinum or steel.

Because drive wire 2 has to course through sinuous conduits in the body it must have the appropriate length for its particular application. For example, when the treatment catheter is used to treat the coronary arteries of the heart, drive wire 2 may be longer than 1 m. Correspondingly, if the treatment catheter is used to treat at a locus closer than the entry point of the treatment wire into the body, drive wire 2 may be shorter than 1 m.

For use in the coronary arteries of the heart, at a point anywhere from 5 cm to 46 cm, preferably from 10 cm to 36 cm, and more preferably from 15 cm to 22 cm, from distal end 4, drive wire 2 has neck area 5. Depending upon the specific area targeted for treatment the location of neck area 5 may vary although it will generally be located closer to distal end 4 relative to the full length of treatment wire 1. Beginning at the proximal end of neck area 5, drive wire 2 is ground to a smaller diameter so that the portion of drive wire 2 that emerges from the neck area has a reduced diameter. For a drive wire 2 made out of nitinol the reduced diameter could be from 0.007" to 0.015", preferably from 0.009" to 0.013", and more preferably from 0.010" to 0.011".

The diameter of drive wire 2 is reduced through centerless grinding with a friction wheel. Care should be taken during the grinding procedure through the use of coolants and/or by reducing the grinding speed to ensure that the resultant heating does not alter the properties of the material of drive wire 2.

Although not necessary, it is beneficial to have neck area 5 transition from the larger diameter of the proximal region to the smaller diameter of the distal region through a gradual taper. This reduces the stress applied to the attachment area of tube 6 to drive wire 2. Thus, neck area 5 would consist of a taper and could span a region having a length from 1 cm to 10 cm, preferably from 2.5 cm to 7 cm, and more preferably 4 cm to 6.5 cm.

Tube 6 is slid around the distal end of drive wire 2 and is attached to drive wire 2 in neck area 5. Tube 6 has an inner diameter that is slightly larger than the diameter of drive wire 2 distal to neck area 5. For example, if a nitinol tube 6 is used in conjunction with a nitinol wire the inner diameter of tube 6 could be larger than the diameter of portion of drive wire 2 distal to neck area 5 by 0.00025" to 0.003", preferably by 0.0004" to 0.002", and more preferably by 0.0005" to 0.0015".

Because of the differential in the diameter of drive wire 2 between the proximal and distal regions of neck area 5, the proximal end of tube 6 will rest in a light press fit relationship with drive wire 2 somewhere along neck area 5. The proximal end of tube 6 is then secured to drive wire 2 in order to achieve the desired integrity that treatment wire 1 needs as it courses through the sinuous conduits of the body. To achieve this, the proximal end of tube 6 can be welded, soldered or attached by any other appropriate means to neck area 5. In the preferred embodiment, tube 6 is circumferentially laser welded around drive wire 2 where the proximal end of tube 6 rests in a light press fit relationship with neck area 5.

Tube 6, which occupies the distal section of treatment wire 1, is approximately 10.0 cm to 30.0 cm long, preferably 15.0 cm to 25.0 cm, and more preferably 19.5 to 21.0 cm. Neck area 5 is placed on treatment wire 1 is such a way as to have the distal end of treatment wire 1 terminate proximately to the distal end of tube 6 to form a cavity 7 that is to receive the treating material. Cavity 7 is preferably 1 mm to 40 mm long, preferably 22 mm to 36 mm long, and more preferably 26 mm to 30 mm long.

The treating material may be any substance that may need to be carried by treatment wire 1 in order to treat a patient. Such materials may be pharmaceutical compounds or elements, or radioactive substances. In one embodiment of treatment wire 1, radioactive isotopes of iridium, phosphorus, tungsten, or terbium can be used, among others, for the delivery of irradiation in the treatment of restenosis.

If an afterloader is used to deploy treatment wire 1, the placement of neck area 5 and the length of tube 6 must be such that any portion distal to the proximal end of neck area 5 does not engage the spool or drive mechanism when the wire is fully retracted into the afterloader. The same would hold true for any other deployment method that would use a spool to store treatment wire 1 when not in use. This prevents any strong compressive forces from being applied on tube 6 that could cause it to collapse.

The distal end of drive wire 2 should be ground before the assembly of the wire so that it is deburred or terminates in a rounded shape so as to relieve stresses that occur as tube 6 and drive wire 2 bend in that area. The distal end of tube 6 can be sealed through the use of plug 8, whose purpose is to retain the treating material in cavity 7 and to avoid any loss of or contamination by the treating material. Plug 8 is preferably rounded and is inserted at the distal end of cavity 7. Plug 8 can be tightly sealed by soldering, welding, or using other known methods in the art. If plug 8 is to be welded, it would preferably be composed from the same material as tube 6. Although the use of a plug 8 reflects the preferred embodiment, cavity 7 can also be sealed through welding, soldering, or the use of sealants.

Because the manufacturing process can affect the properties of treatment wire 1, it is important to verify as part of the manufacture of the wire the material properties including metallurgy, surface finish, oxidation, and, in the case of shape-memory/superelastic materials, the transformation temperature. Subjecting the wire to repeated cycles of stress that simulate the stress cycles to which the wire will be subjected in use is important to detect otherwise unseen characteristics that may adversely affect its performance.

If shape-memory/superelastic material is used to construct treatment wire 1, care should be taken that the material have the proper properties. Although other metallurgical processes may be possible for imparting treatment wire 1 with different properties over its length, for ease of manufacture, the preferred method is to heat treat the distal portion of treatment wire 1 so as to at least partially disable its superelastic properties at or below normal body temperature (approximately 37° C.).

Shape-memory/superelastic bulk wire and tubing can be purchased commercially with both a transformation temperature and a recovery temperature below approximately 25° C. Accordingly, at room or body temperature, the wire exhibits shape-memory (and the related superelasticity below the transformation temperature). It is important that the wire's transformation temperature be below normal body temperature (approximately 37° C.). The wire and tubing should preferably have a remembered shape of being substantially straight.

In the preferred embodiment, the shape-memory/superelastic material is nitinol having a composition of about 55% to 56% nickel and 45% to 44% titanium respectively. Of course minor trace elements are also present in the alloy. This composition can of course be varied in order to obtain different properties in treatment wire 1.

Alloys having shape-memory/superelastic characteristics typically exist in two phases —a martensitic phase and an austenitic phase. The martensite is stable at relatively low temperatures; the austenite is stable at temperatures higher than the martensite.

Shape-memory is the ability of certain alloys, such as nitinol, to return to their original shape when heated over a certain temperature. Superelasticity is the related property of such a material where even if strained beyond its yield point such that it appears to have undergone plastic deformation, the material returns to its original shape when the external stress is removed.

In the austenitic phase, the crystal structure is body-centered cubic. When cooled below its transformation temperature, the austenitic structure undergoes a diffusion-less shear transformation to a twinned martensite crystal structure. In the martensitic phase, the twinned structure can be mechanically deformed. This deformation remains as long as the material remains below its transformation temperature. When the deformed martensitic structure, however, warms through its transformation temperature, it returns immediately to the austenitic form and if unrestrained it will return to its original shape. This constitutes shape-memory.

In the austenitic phase when stress is applied to a material such as nitinol exhibiting superelastic characteristics at a temperature above which the austenite is stable (i.e., above the transformation temperature), the material initially deforms elastically until the stress level causes a stress-induced transformation from the austenitic phase to the martensitic phase. As the phase transformation continues, the alloy undergoes significant increases in strain with little or no corresponding increases in stress until the transformation in the stressed region is complete. Continued stress causes the martensitic phase to continue the deformation at first elastically and eventually plastically. Once there is plastic deformation of the stress-induced martensite the material will have some permanent residual deformation.

If the stressing load is removed before permanent deformation sets in, the stress-induced martensite elastically recovers and transforms back to austenite. After this transformation is complete, there is further elastic recovery of the austenite and the material returns to substantially its original shape. This ability of shape-memory alloys to incur significant strain at relatively constant stress when under load and to recover from the deformation upon removal of the load is referred to as superelasticity or pseudoelasticity.

It has been observed that the heat treatment of a portion of such a superelastic wire yields a result akin to elevating the transformation temperature. Thus, any portion of a wire that has received such heat treatment becomes less superelastic. With the plastic deformability increased over that of an alloy operating in its superelastic region, the heat treated material becomes more ductile.

The heat treatment procedure described here has been observed to provide the desired characteristics in nitinol wire having the preferred embodiment composition disclosed above. If different proportions of nickel and titanium or altogether different alloys are used for the construction of treatment wire 1, it is understood that the temperatures and duration for the heat treatment may vary.

If shape-memory/superelastic material is used to construct treatment wire 1, the heat treatment of the distal portion of treatment wire 1 will render it more plastic than the rest of the wire. This increased deformability is desirable when treatment wire 1 is deployed within the body for treatment. When the distal end of treatment wire 1 is deformed as it is fed through the catheter toward the treatment locus, it does not have the same restorative tendency as the superelastic portion and, therefore, has a better tendency to follow the catheter with less catheter displacement. By virtue of its increased deformability, the distal end has less tendency to stress the body channel near the treatment locus, thereby reducing incidental trauma. It also has less tendency to puncture or gouge the catheter, thereby becoming obstructed and causing the procedure to be terminated.

If an afterloader is used to deploy treatment wire 1, the ductile distal end of the wire must not be so long as to engage the spool mechanism when the wire is fully retracted into the afterloader. The same would hold true for any other deployment method that would use a spool to store treatment wire 1 when not in use. If, however, treatment wire 1 is used in a tissue where the body passages are particularly tortuous near the treatment locus (e.g., coronary arteries), the ductile distal end of treatment wire 1 should also be sufficiently long so that the superelastic portion of the wire does not enter them (e.g., coronary arteries) during the procedure. Accordingly, the ductile portion should extend back from the distal tip of treatment wire 1 about 2.5 cm to 31 cm, preferably about 12.5 cm to 23 cm, and more preferably, for use for example in the coronary arteries, about 17 cm.

The heat treatment of the nitinol may vary but some general principles have been discovered. Below approximately 300° C. the transformation and recovery temperatures of the wire are relatively unaffected. On the other hand, if treated above approximately 450° C., it is difficult to reliably impart the desired ductility properties on the heat treated portion of the nitinol wire assembly.

The heat treatment of the distal end of treatment wire 1 can occur in several ways. For example, only tube 6 can be heat treated so as to lose its superelastic properties. Although the ground portion of drive wire 2 that is within tube 6 will retain is superelasticity, the distal end of treatment wire 1 will still behave as a whole as generally not superelastic because of the effect of the nonsuperelastic tube 6. This is especially true when, as would often occur, the cross-sectional area of tube 6 is larger than the cross-sectional area of the ground distal end of drive wire 2. Alternatively, the entire distal end of treatment wire 1, after tube 6 has been assembled with drive wire 2, can be heat treated as a whole. Finally, if desirable for a particular application, the ground portion of drive wire 2 could be heat treated before assembly with an untreated tube 6. The treatment source is not loaded into cavity 7 until after final assembly and heat treatment. Then plug 8 is used to tightly seal the hole.

The heat treatment occurs by placing the desired portion to be treated in a metallurgical oven, which has been preheated to a temperature in a range from 300° C. to 450° C., preferably in a range from 350° C. to 400° C., and more preferably in a range from 370° C. to 380° C. If only tube 6 is treated, it can be placed in its entirety in the oven. If the distal portion of the drive wire 2/tube 6 assembly or the distal portion of drive wire 2 is treated, it can be placed in the oven through a small hole drilled in the door of the metallurgical oven. The hole only needs to be slightly larger than the wire. The heat treatment should last about 200 to 500 minutes, preferably about 220 to 340 minutes, and more preferably about 240 to 280 minutes. Upon completion of the heat treatment the treated portion of the nitinol assembly is preferably cooled at a rate of 1° C. per minute until it reaches room temperature. Simple air cooling to room temperature, however, has also been observed to be adequate.

FIG. 6 shows an alternative embodiment of this invention. The construction of treatment wire 9 is similar to that of treatment wire 1 except that instead of tube 6 a tightly wound coil 12 is attached at neck area 11 of drive wire 10 and surrounds the distal portion of drive wire 10. All dimensions of drive wire 10, the placement and dimensions of neck area 11, and the dimensions of coil 12 are the same as those of their counterparts in treatment wire 1. Plug 13 is used to seal the treating material in cavity 14, which like cavity 7 is created because the distal end of drive wire 10 terminates proximately to the distal end of coil 12. The dimensions of cavity 14 are the same as those for cavity 7. Moreover, the same materials described for treatment wire 1 may be used for the construction of treatment wire 9, and the same construction techniques should also be used.

The use of coil 12 instead of tube 6 provides some additional ductility to the distal end of treatment wire 9. If shape-memory/superelastic materials are used, as was the case with treatment wire 1, the heat treatment process described above can be used to further increase the ductility of the distal portion of treatment wire 9.

Because coil 12 in treatment wire 9 does not hermetically seal the treating material from the body of the patient, the treating material has to be encapsulated and sealed before it is placed in cavity 14. Methods for sealing treating materials are known in that art and some are described in the references incorporate herein.

Although a preferred embodiment and method of the present invention has been described, it will be apparent from the foregoing description to those skilled in the field of the invention that variations and modifications of the invention may be implemented without departing from the spirit and scope of the invention. Accordingly, it is understood that all such variations and modifications are believed to fall within the scope of the invention as defined in the appended claims.

REFERENCES

The following references, to the extent that they provide exemplary procedural or other details supplementary to those set forth herein, are specifically incorporated herein by reference.

U.S. Pat. No. 4,819,618; U.S. Pat. No. 4,861,520; U.S. Pat. No. 5,084,002; U.S. Pat. No. 5,141,486; U.S. Pat. No. 5,199,939; U.S. Pat. No. 5,238,004; U.S. Pat. No. 5,282,781; U.S. Pat. No. 5,503,614.

What is claimed is:

1. A flexible treatment device for treating a selected site within a patient's body comprising:

a flexible, predominantly solid, thin elongate wire having an outer diameter, a proximal end and a distal end, the wire having a tapered neck area between the proximal end and the distal end with the outer diameter of the wire being smaller between the neck area and the distal end than between the neck area and the proximal end;

the wire being constructed from approximately 56% nickel and approximately 44% titanium;

a flexible, hollow, elongated tube having a proximal end, a distal end, an outer diameter and an inner diameter with the outer diameter of the tube being substantially the same as the outer diameter of the wire between the neck area and the proximal end of the wire;

the tube being constructed from approximately 56% nickel and approximately 44% titanium;

the inner diameter of the tube being slightly larger than the outer diameter of the wire between the neck area and the distal end of the wire;

the tube and the wire being operatively coupled to form an elongate assembly having a proximal portion and a distal portion with the proximal end of the tube being laser welded to the neck area so as to encase the wire between the neck area and the distal end of the wire, and the distal end of the tube extending beyond the distal end of the wire to form a cavity;

the distal portion of the elongate assembly being heat treated to be more ductile relative to the proximal portion of the elongate assembly; and a treating material being secured within the cavity.

2. The device of claim 1, wherein substantially all of the proximal portion of the elongate assembly has a transition temperature below approximately 37° C.

3. The device of claim 2, wherein the distal portion of the elongate assembly is heat treated by inserting the distal portion in an oven preheated to a range of approximately 300° C. to approximately 450° C. and keeping the distal portion in the oven for over 200 minutes.

4. The device of claim 1, wherein substantially all of the proximal portion of the elongate assembly has a transition temperature below approximately 25° C.

5. The device of claim 4, wherein the distal portion of the elongate assembly is heat treated by inserting the distal portion in an oven preheated to a range of approximately 300° C. to approximately 450° C. and keeping the distal portion in the oven for over 200 minutes.

6. The device of claim 1, wherein the treating material is radioactive.

7. The device of claim 1, wherein the treating material is secured within the cavity by an end plug.

8. A flexible treatment device for treating a selected site within a patient's body comprising:

a flexible, predominantly solid, thin elongate wire having an outer diameter, a proximal end and a distal end, the wire having a tapered neck area between the proximal end and the distal end with the outer diameter of the wire being smaller between the neck area and the distal end than between the neck area and the proximal end;

the wire being constructed from approximately 56% nickel and approximately 44% titanium;

a flexible, hollow, elongated tube having a proximal end, a distal end, an outer diameter and an inner diameter with the outer diameter of the tube being substantially the same as the outer diameter of the wire between the neck area and the proximal end of the wire;

the tube being constructed from approximately 56% nickel and approximately 44% titanium;

the inner diameter of the tube being slightly larger than the outer diameter of the wire between the neck area and the distal end of the wire;

the tube and the wire being operatively coupled to form an elongate assembly with the proximal end of the tube being laser welded to the neck area so as to encase the wire between the neck area and the distal end of the wire, and the distal end of the tube extending beyond the distal end of the wire to form a cavity;

the tube being heat treated to be more ductile relative to the wire; and a treating material being secured within the cavity.

9. The device of claim 8, wherein substantially all of the wire has a transition temperature below approximately 37° C.

10. The device of claim 9, wherein the tube is heat treated by inserting it in an oven preheated to a range of approximately 300° C. to approximately 450° C. and keeping the tube in the oven for over 200 minutes.

11. The device of claim 8, wherein substantially all of the wire has a transition temperature below approximately 25° C.

12. The device of claim 11, wherein the tube is heat treated by inserting it in an oven preheated to a range of approximately 300° C. approximately 450° C. and keeping the tube in the oven for over 200 minutes.

13. The device of claim 8, wherein the treating material is radioactive.

14. The device of claim 8, wherein the treating material is secured within the cavity by an end plug.

15. A flexible treatment device for treating a selected site within a patient's body comprising:

a flexible, predominantly solid, thin elongate wire having an outer diameter a proximal end and a distal end, the wire having a neck area between the proximal end and the distal end with the outer diameter of the wire being smaller between the neck area and the distal end than between the neck area and the proximal end;

a flexible, hollow, elongated tubular member having an inner diameter, a proximal end, and a distal end;

the inner diameter of the tubular member being slightly larger than the outer diameter of the wire between the neck area and the distal end of the wire;

the proximal end of the tubular member being operatively coupled to the neck area so as to encase the wire between the neck area and the distal end of the wire, and the distal end of the tubular member extending beyond the distal end of the wire to form a cavity; and a treating material secured within the cavity.

16. The invention of claim 15, wherein the proximal end of the tubular member is soldered to the neck area of the wire.

17. The invention of claim 15, wherein the proximal end of the tubular member is welded to the neck area of the wire.

18. The invention of claim 15, wherein the wire and the tubular member are constructed from a superelastic alloy having a transition temperature below approximately 37° C.

19. The invention of claim 18, wherein the tubular member is a tube.

20. The invention of claim 18, wherein the tubular member is a coil.

21. The invention of claim 18, wherein the proximal end of the tubular member is laser welded to the neck area of the wire.

22. The invention of claim 15, wherein the treating material is radioactive.

23. The invention of claim 18, wherein the treating material is secured within the cavity by an end plug.

24. The invention of claim 15, wherein the wire and the tubular member form an elongate assembly, having a distal end and a proximal end, the wire and the tubular member being constructed from a shape-memory/superelastic alloy;

a portion of the elongate assembly at the distal end of the elongate assembly having a transition temperature above approximately 37° C.; and substantially all of the remainder of the elongate assembly having a transition temperature below approximately 37° C.

25. The invention of claim 24, wherein the proximal end of the tubular member is soldered to the neck area of the wire.

26. The invention of claim 24, wherein the proximal end of the tubular member is welded to the neck area of the wire.

27. The invention of claim 24, wherein the proximal end of the tubular member is laser welded to the neck area of the wire.

28. The invention of claim 24, wherein the tubular member is a tube.

29. The invention of claim 24, wherein the distal portion of the elongate assembly is from 1" to 12" in length.

30. The invention of claim 24, wherein the distal portion of the elongate assembly is from 3" to 9" in length.

31. The invention of claim 24, wherein the recovery temperature of the distal portion of the elongate assembly is altered by heat treatment comprising exposing the distal portion to a temperature of 300° C. to 450° C. for 200 to 500 minutes.

32. The invention of claim 24, wherein the superelastic alloy comprises approximately 55.6% nickel and approximately 44.4% titanium.

33. The invention of claim 27, wherein the superelastic alloy comprises approximately 55.6% nickel and approximately 44.4% titanium.

34. The invention of claim 31, wherein the superelastic alloy comprises approximately 55.6% nickel and approximately 44.4% titanium.

35. A flexible treatment device for treating a selected site within a patient's comprising:

- a flexible, predominantly solid, thin elongate wire composed of a superelastic alloy having a proximal end and a distal end;
- a flexible, hollow, elongated tube composed of a superelastic alloy having a proximal end and a distal end;
- the proximal end of the tube being operatively coupled to a coupling point on the wire short of the distal end of the wire so as to encase the wire between the coupling point and the distal end of the wire and forming a wire/tube assembly wherein the distal end of the tube extends beyond the distal end of the wire to form a cavity;
- the wire/tube assembly having a distal end and a proximal end; and
- the distal end of the wire/tube assembly is metallurgically treated to have increased deformability relative to the proximal end of the wire/tube assembly.

36. The invention of claim 35, wherein the wire and the tube are constructed from an alloy comprising approximately 55.6% titanium and approximately 44.4% nickel.

37. The invention of claim 36, wherein the distal end of the wire/tube assembly is heat treated to make it more ductile relative to the proximal end of the wire/tube assembly.

38. A flexible treatment device for treating a selected site within a patient's comprising:

- a flexible, elongate wire composed of a superelastic alloy having a proximal end and a distal end;
- a flexible, hollow, elongated tube composed of a superelastic alloy having a proximal end and a distal end;
- the proximal end of the tube being operatively coupled to a coupling point on the wire short of the distal end of the wire so as to encase a portion of the wire and form a wire/tube assembly having a distal end and a proximal end; and
- the distal end of the wire/tube assembly being treated to be less superelastic relative to the proximal end of the wire/tube assembly.

39. The invention of claim 38, wherein the wire and the tube are constructed from an alloy comprising approximately 56% titanium and 44% nickel.

40. The invention of claim 39, wherein the distal end of the wire/tube assembly is treated to be less superelastic relative to the proximal end of the wire/tube assembly by inserting the distal end in an oven preheated to a range of approximately 300° C. to approximately 450° C. and keeping the distal end in the oven for over 200 minutes.

* * * * *

UNITED STATES PATENT AND TRADEMARK OFFICE
CERTIFICATE OF CORRECTION

PATENT NO.   :   5,782,741

DATED        :   July 21, 1998

INVENTOR(S)  :   Anthony J. Bradshaw, Kenneth M. Bueche

It is certified that error appears in the above-identified patent and that said Letters Patent is hereby corrected as shown below:

Col. 1, ln. 22 delete "5,141,486" and insert --5,141,476--.

Col. 1, ln. 24 delete "5,141,486" and insert --5,141,476--.

Col. 4, ln. 43 delete "terbium" and insert --ytterbium--.

Col. 8, ln. 14 delete "5,141,486" and insert --5,141,476--.

Col. 11, ln. 17 after "patient's" insert --body--.

Col. 12, ln. 3 after 55.6% delete "titanium" and insert --nickel--.

Col. 12, ln. 4 after 44.4% delete "nickel" and insert --titanium--.

Col. 12, ln. 10 after "patient's" insert --body--.

UNITED STATES PATENT AND TRADEMARK OFFICE
CERTIFICATE OF CORRECTION

PATENT NO. : 5,782,741

DATED : July 21, 1998

INVENTOR(S) : Anthony J. Bradshaw, Kenneth M. Bueche

It is certified that error appears in the above-identified patent and that said Letters Patent is hereby corrected as shown below:

Col. 12, ln. 25 after 56% delete "titanium" and insert --nickel--.

Col. 12, ln. 26 after 44% delete "nickel" and insert --titanium--.

Signed and Sealed this

Twentieth Day of April, 1999

Attest:

Q. TODD DICKINSON

Attesting Officer

Acting Commissioner of Patents and Trademarks